United States Patent
Bergner

(10) Patent No.: US 10,429,674 B2
(45) Date of Patent: Oct. 1, 2019

(54) SAFETY GLASSES HAVING OPTICALLY CORRECTIVE LENSES

(71) Applicant: Walter Bergner, Bad Kreuznach (DE)

(72) Inventor: Walter Bergner, Bad Kreuznach (DE)

( * ) Notice: Subject to any disclaimer, the term of this patent is extended or adjusted under 35 U.S.C. 154(b) by 0 days.

(21) Appl. No.: 15/034,045

(22) PCT Filed: Oct. 31, 2014

(86) PCT No.: PCT/DE2014/100386
§ 371 (c)(1),
(2) Date: Jun. 27, 2016

(87) PCT Pub. No.: WO2015/062587
PCT Pub. Date: May 7, 2015

(65) Prior Publication Data
US 2016/0299358 A1    Oct. 13, 2016

(30) Foreign Application Priority Data

Nov. 4, 2013 (DE) .................... 20 2013 104 927 U

(51) Int. Cl.
*G02C 9/00* (2006.01)
*G02C 3/00* (2006.01)
(Continued)

(52) U.S. Cl.
CPC ................ *G02C 9/00* (2013.01); *A61F 9/025* (2013.01); *G02C 1/10* (2013.01); *G02C 3/003* (2013.01);
(Continued)

(58) Field of Classification Search
CPC . G02C 9/00; G02C 3/00; G02C 3/003; G02C 1/06; G02C 1/10; G02C 1/08;
(Continued)

(56) References Cited

U.S. PATENT DOCUMENTS

| 2,799,862 A | 7/1957 | Rowe |
| 4,317,240 A | 3/1982 | Angerman et al. |

(Continued)

FOREIGN PATENT DOCUMENTS

| DE | 299 19 010 | 3/2000 |
| FR | 2 592 281 A1 | 7/1987 |

(Continued)

OTHER PUBLICATIONS

International Search Report for corresponding International PCT Application No. PCT/DE2014/100386 dated Apr. 8, 2015.

*Primary Examiner* — Jie Lei
(74) *Attorney, Agent, or Firm* — Hauptman Ham, LLP

(57) ABSTRACT

Safety glasses having integrated correction lenses, wherein connecting means in the style of retaining frames are arranged in or on the safety glasses in order to accommodate the correction lenses, comprising adapter rings as compensating bodies between the curvature of the outer contour of the safety glasses and the curvature of the inserted correction lenses, wherein the correction lenses of different power are matched to the adapter rings in a uniformly accurately fitting manner at the periphery of the correction lenses in the curvature and shape of the correction lenses and different powers of correction lenses can be inserted into the adapter rings in the space between the safety glasses and the inner curvature of the adapter rings, wherein the adapter rings are thicker in the nasal region and taper temporally, approximately in a wedge shape.

8 Claims, 3 Drawing Sheets

(51) Int. Cl.
*G02C 5/02* (2006.01)
*G02C 5/14* (2006.01)
*A61F 9/02* (2006.01)
*G02C 11/08* (2006.01)
*G02C 1/00* (2006.01)

(52) U.S. Cl.
CPC .............. *G02C 5/02* (2013.01); *G02C 5/143* (2013.01); *G02C 11/08* (2013.01); *A61F 2009/021* (2013.01)

(58) Field of Classification Search
CPC . G02C 7/16; G02C 11/08; G02C 5/00; G02C 5/14; G02C 5/02; G02C 5/143; A61F 9/025; A61F 9/02; A61F 2009/021
USPC ....... 351/57, 86, 62, 92, 154, 178; 2/13, 6.3, 2/426, 441, 442, 443
See application file for complete search history.

(56) References Cited

U.S. PATENT DOCUMENTS

| | | | |
|---|---|---|---|
| 4,796,986 A * | 1/1989 | Gowdy, Jr. | ............... G02C 1/10 351/149 |
| 5,428,407 A | 6/1995 | Sheffield | |
| 6,292,955 B1 | 9/2001 | Anton | |
| 2007/0024806 A1* | 2/2007 | Blanshay | ................. G02C 9/00 351/62 |
| 2008/0186445 A1 | 8/2008 | Van Atta | |
| 2011/0001922 A1 | 1/2011 | Sheldon | |

FOREIGN PATENT DOCUMENTS

| | | |
|---|---|---|
| WO | 99/54000 A1 | 10/1999 |
| WO | 2004/031810 A2 | 4/2004 |

* cited by examiner

SAFETY GLASSES HAVING OPTICALLY CORRECTIVE LENSES

The invention relates to protective glasses, in particular protective eye wear for the workplace or sunglasses, and the connection thereof to optically corrective lenses, which may be arranged on the protective glasses from the inside or the outside.

For this invention, the term protective glasses is understood to mean, in principle, glasses having optically non-corrective lenses. Therefore, protective glasses within the context of the invention, on the one hand, are to be understood to mean protective eye wear for the workplace which protects the wearer's eyes, for example, during processes involving swarf, sparks or the like. Also intended however, on the other hand, are sports glasses (or goggles) as are used, for example, by cyclists or skiers in order to protect the wearer's eyes against flying particles. Finally, sunglasses also come into the equation as glasses which protect against excessively intensive irradiation of light into the wearer's eyes.

For these protective glasses, it is usually the case that the lenses of the protective glasses do not correct the wearer's sight defects in the form of short sightedness or long sightedness. For the glasses wearer who has poor eyesight and requires protective glasses for work or leisure purposes, there are different alternatives, the least advantageous of these being to dispense with the use of protective glasses.

A widely practiced solution is that of wearing protective glasses in addition over normal glasses having optically corrective lenses, provided the size of the protective glasses allows this to be done. However, this can be fairly uncomfortable, and, in addition, a desirable tight seal between the protective glasses and the wearer's face is impeded by the glasses having optically corrective lenses being worn in addition. This is a makeshift solution which is ruled out from the outset for applications based on dynamics, for example sport.

The more sensible solution is to provide the protective glasses with optically corrective lenses. For example in the case of sunglasses, it is known to use directly optically corrective lenses with, at the same time, strong tinting.

This solution, however, has limits placed upon it by the shapings which are desired for protective glasses nowadays. Much store is set by a shape which has pronounced curvature, butts closely against the wearer's head contour and is produced entirely from plastics material. It is not readily possible for correction lenses to be integrated directly in these protective glasses.

As an alternative, it is known in the prior art to use correction lenses in protective glasses, either inserted into appropriate mounts in the, for example, plastics-material glasses or fitted on the front side or rear side of the protective glasses. The documents which now follow form examples of prior art relevant to the present invention.

DE 1 208 909 discloses protective glasses which are made of plastics material and which have formed on the inner surface of the protective lens an approximately annular elevation, which serves as a frame for a correction lens which is to be inserted. The correction lenses here should be inserted in a rotatable manner in the frame.

DE 2 923 798 likewise describes protective glasses, a correction lens being fastened on each of the see-through parts thereof. It is described here that said correction lens is adhesively bonded to the inner side of the see-through part.

AT 328 205 describes protective glasses which can be worn, in particular, for sport, wherein the face panel contains openings into which correction lenses can be inserted directly. These openings may have specific shapings in order also to allow a form-fitting connection of the correction lenses in the plastics-material frame. It is additionally disclosed here that the peripheries of the correction lenses are adhesively bonded or welded to the peripheries of the openings of the face panel.

FR 2 592 281 discloses that a correction lens is fitted in a form-fitting manner into a carrier body of the protective glasses. Appropriate lugs are provided for this purpose, and said lugs engage in corresponding mounts in the protective glasses. It is therefore also the case that this document discloses a direct connection between the correction lenses and the protective glasses.

Finally, U.S. Pat. No. 4,796,986 discloses that the rear side of the protective glasses has arranged on it a corresponding retaining shell, into which correction lenses can be inserted. This document therefore discloses the arrangement of the correction lenses directly on the rear surface of the protective glasses.

These disclosed solutions demonstrate overall that the basic idea of placing correction lenses directly on or in protective glasses has been considered on a large number of previous occasions, but they have in common the disadvantage that they require a high level of production outlay and are therefore not cost-effective. In addition, they continue to be based on protective glasses which tend to be planar, wherein the subject matter of the invention relates to shapings which have pronounced curvature and present the use of correction lenses in these protective glasses with new challenges.

A further approach which is common in the prior art is for conventional glasses provided with correction lenses to have additional lenses plugged or fastened on them in order to extend the functionalities of the corrective glasses. This aspect, however, relates more or less exclusively to the arrangement of sunglasses lenses in front of conventional glasses, as is also described in the prior art, for example, in DE 202011003548 U1 and DE 202006017053 U1.

These are usually provisional and only temporarily usable solutions, of which the sole purpose is to provide an inexpensive replacement for separate sunglasses. Disadvantageously, these are usually unstable and optically insufficient solutions. Using these solutions in the field of protective glasses within the context of the invention is not encouraged here, since a conventional glasses frame is unsuitable for this purpose.

It is therefore an object of the invention to create protective glasses which can be equipped straightforwardly and cost-effectively with optically corrective lenses.

This object is achieved according to the invention by an adapter ring which, arranged on the protective glasses, accommodates the correction lens.

The first embodiment is a correction lens placed on the inside. This embodiment makes provision for an adapter ring to be inserted into the inside of protective glasses, or also for example sunglasses, the adapter ring then establishing the connection to the correction lens. The background here is that use is increasingly being made of protective glasses, or also sunglasses, which have their outer contour adapted to a pronounced extent to the curvature of a person's head, that is to say that the glasses curve in abutment against the head. These extreme curvatures in the glasses, in contrast to relatively planar glasses retained in glasses frames, makes the task of machining these glasses for correction lenses an extremely complex one.

If for example modern sports glasses having tinted lenses are to be subject to correction grinding, such machining can give rise to costs of up to € 1000. The advantage of the disclosed solution can therefore be considered that of it being possible to utilize standard protective glasses, or also sunglasses, into which likewise standard, inexpensive correction lenses can be inserted.

The adapter ring here is of wedge-shaped design and, arranged in the protective glasses, is thicker in the nose region and tapers at the temples. As a result, the corrective optical lens retained in the adapter ring is angled into the face plane in relation to the basic structure of the protective glasses, and this ensures that the wearer's axis of vision is more or less perpendicular to the correction lens, and problematic distortions for the wearer's eye are therefore avoided. It is thus possible for the protective glasses to butt closely against the head and nevertheless the correction lenses to be arranged so that they are oriented in a manner similar to a conventional glasses arrangement.

The adapter ring has the additional function of compensating for two different curvatures in relation to one another. This means that the aim of the adapter ring is therefore to compensate for the curvature of the contour of the protective glasses, or sunglasses, and the curvature of the glasses lens inserted.

At the same time, the intention is thus to achieve the situation where it is possible to utilize a standard adapter ring. The adapter ring is standardized in terms of curvature of abutment against the protective glasses and can thus be adhesively bonded again and again to a specific standard pair of protective glasses, or inserted again and again into the same. On the other hand, however, it is also the case that the curvature in the direction of the inner side, into which the correction lens is fitted, is standardized, which, in turn, corresponds with the so-called facet, with appropriately standardized curvature, on the correction lens which is to be inserted. Also relevant to the invention, therefore, are the standard-facet correction lenses designed specifically for this solution, since both plus lenses and diffusion lenses or concave lenses have to have the same facet.

This means that both the outer contour and the inside edge shaping and curvature of the adapter ring are designed such that the latter allows fully planar abutment of the correction lens. The facet of the correction lens, for this purpose, has its curvature and its shaping coordinated in a precisely fitting manner with said adapter ring and the shaping thereof.

Against this background, it is likewise relevant that, contrary to the conventionally used thermoplastic materials, into which the lenses can be inserted on account of the plastic deformability, the invention utilizes thermoset materials for the adapter rings, since it is very much the case that deformation is not to take place. As already described, the precisely fitting characteristic, then, is at odds with the flexibile deformability in the prior art.

As a result, correction lenses of different thicknesses and curvatures can be fitted on said adapter ring and adhesively bonded or welded thereto. It is quite deliberately intended here for a space to remain between the protective glasses worn and the fitted correction lens, enclosed by the adapter ring, since it is thus possible for differently shaped correction lenses to be inserted in always the same adapter ring.

Since the free space between the correction lens and protective glasses is tightly sealed, it is not disadvantageous in any way. A specific embodiment here makes provision for the correction lenses to be fitted in a specific space with low temperature and air humidity, it therefore being the case that the air space enclosed between the correction lens, adapter ring and protective glasses correspondingly has no moisture enclosed in it which could result, for example in the event of a change in temperature, in misting. As an alternative, the intention is for the air in the space between the correction lens and protective glasses to be evacuated, that is to say to be extracted by way of possibly a valve inserted into the adapter ring, as a result of which it is likewise the case that there is no longer any moisture present in the interspace.

The difference in the prior art therefore, on the one hand, is that there is deliberately a free space connected between the protective glasses and correction lens. This allows variable usage of a wide variety of different curved glasses lenses. On the other hand, the correction lenses have a specific facet integrated in their periphery, which is configured for resting on the upper side of the adapter ring. This means that the correction lens, rather than being pushed into the adapter ring, is merely positioned thereon and then adhesively bonded or welded thereto. This has the great advantage that this can take place in a very controlled manner and with defined positioning. At the same time, it is thus ensured that it is possible to use any lens, the only requirement being for the lenses relevant here to have identical facets, since it is therefore possible for a multiplicity of lenses to be introduced.

In addition this has production-related advantages, since it is thus possible to utilize any desired protective glasses which are already in existence, the only requirement being for the appropriate adapter rings to be specifically made in order for said facets to be introduced into the lenses.

A further technical idea is that it is also possible for the positioning of the adapter ring on the protective glasses to be assisted by technical means, that is to say that the adapter ring is not simply attached via adhesive bonding. This can be achieved by for example plug-in lugs being arranged on the underside of the adapter ring, in the direction of the protective glasses, it being possible for said plug-in lugs to be plugged into corresponding bores in the protective glasses. The position of the correction lenses on the protective glasses is predefined by, for example, two retaining lugs and two bores. Preliminary fixing would be achieved in addition, this then facilitating adhesive bonding. Other structural solutions, however, are also conceivable here in relation to how it is possible to predefine this connection and positioning.

In the case of the alternative embodiment of a correction lens inserted at the front, use is not made of an adapter ring; rather, there is a recess provided in the protective glasses, or sunglasses, and an entire lens is inserted into said recess. In a manner analogous to the design of the adapter ring, the recess contains a step, which is milled into the protective glasses, and there is a correspondingly adapted facet on the glasses lens, as a result of which, here too, the glasses lens is inserted in a precisely fitting manner into the corresponding step by means of the facet.

In a further alternative embodiment, the adapter rings are not fitted into the protective glasses subsequently in the form of separate structural elements; rather, the protective glasses created are ones which already have adapter rings incorporated on the inside at the production stage, in particular production using plastics materials. This is an ideal solution since the manual outlay for producing the protective glasses can thus be further reduced. The adapter rings which are thus already present as an integral constituent part of the protective glasses can have the lenses fitted in directly, as described, by way of the standard regions of connection between an optical correction lens and adapter ring.

An embodiment with an adapter ring inserted into the inside of the protective glasses will be described in more detail hereinbelow. The adapter ring in combination with the special faceting serves for the installation and combined assembly of optical structures without refractive action and structures with refractive action, wherein the structures without optical action, that is to say the basic structure of the protective glasses, can range from a planar, infinite radius of curvature, to spherical, radius of curvature of 1000 mm to 400 mm.

The structures with refractive action may have spherical surfaces or cylindrical surfaces or combined spherical/cylindrical surfaces.

The adapter ring of any desired shape and size with a defined periphery or crosspiece height, e.g. 4 mm, and a defined periphery or crosspiece width, e.g. 3 mm, is adapted to the basic structure such that it replicates, on its front side, the spherical curvature of the basic structure, and it can therefore be adhesively bonded, welded or molded thereto in an absolutely sealed and stressing-free manner.

That side of the adapter ring which is directed away from the basic structure is configured such that it likewise can be adapted to a spherical surface in a precisely fitting and absolutely sealed manner. This surface may be planar, with an infinite radius, or have a radius of curvature from 1000 mm to 500 mm. This surface is the front side of an optical lens. The lens has its outer contour configured such that it replicates the shape of the adapter ring.

On that side which is directed toward the basic lens or protective glasses, the optical lens is provided with a facet, which follows or replicates the spherical progression of the rear side of the adapter ring. It is thus possible for the correction lens, applied in a precisely fitting, sealed and stressing-free manner, to be adhesively bonded, welded or molded to the peripheries. The resulting space, formed from the basic structure/protective glasses, adapter ring and correction lens, is an empty space. Contact between the basic structure and correction lens, and also ventilation between the empty space and exterior, is deliberately avoided here.

In an advantageous embodiment of the invention, provision is made for the adapter rings to have their nose regions connected via a bridge, as a result of which the adapter rings themselves already form a basic frame. This frame formed from the adapter rings connected by a bridge either can be inserted into the protective glasses as described above, this having the advantage that all that is required is for an adapter body formed from the 2 connected adapter rings to be fitted in, this amounting to a labor-saving exercise.

As an alternative, it is also possible, however, for said basic frame formed from the adapter rings to form the carrying structure of the protective glasses. Here too, different variations are possible. On the one hand, this adapter frame can be fitted, by way of its bridge, on the bridge of the nose of the person wearing the glasses, wherein either a continuous protective-glasses-lens covering is provided on the front side of the adapter body or a protective-glasses lens can be fitted to the adapter on the left and right in each case, or the adapter body can be fitted into said lenses. In the case of this embodiment, the ear pieces or alternative retaining-strap devices for fastening the protective glasses on the face are arranged laterally in the temple region on the protective-glasses lenses.

In a further alternative embodiment, these carrying elements, such as ear pieces or alternative retaining straps, are likewise arranged on the adapter body formed from the adapter rings and the bridge. This already gives a basic design of a glasses body formed from, for example, ear pieces, the adapter rings and the bridge connecting the same, the lenses of the protective glasses or a continuous protective-glasses-lens body then being fitted thereon.

It should be said here, however, that the glasses in question here are not conventional glasses on which additional lenses, for example in the form of sunglasses lenses, can be fitted for example in a releasable manner. Said embodiment of the adapter body also has the properties according to the invention: outer curvature adapted to the pronounced curvature of the protective glasses; inner curvature adapted to the facet of the optical correction lenses, wherein the already previously explained compensation between the curvature of the protective-glasses lenses and the curvature of the optical correction lenses takes place.

Finally, it is also the case that this solution exhibits the projected development of the optical correction lenses according to the invention in relation to the curvature of the protective glasses, in order to maintain the optical axis of the optical correction lenses in an ideal orientation without the curvature of the protective-glasses lenses having to be changed. To this extent, it is also the case in this embodiment that the adapter rings have the inventive wedge shape from the nose to the temples.

The invention will be described in more detail hereinbelow with reference to a number of figures, in which.

Figure 3:
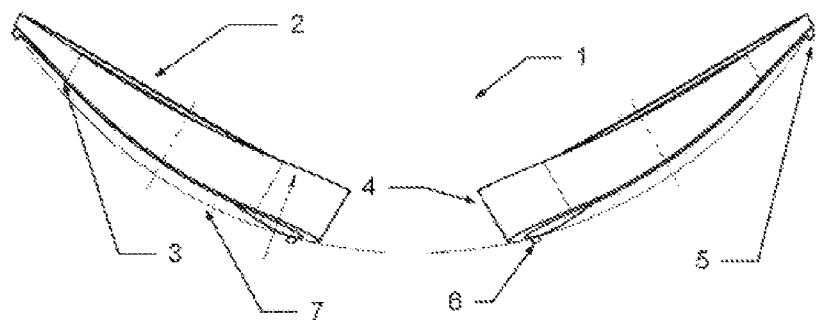
FIG. 3 shows a plan view of the adapter rings 1 according to the invention.
Figure 4:
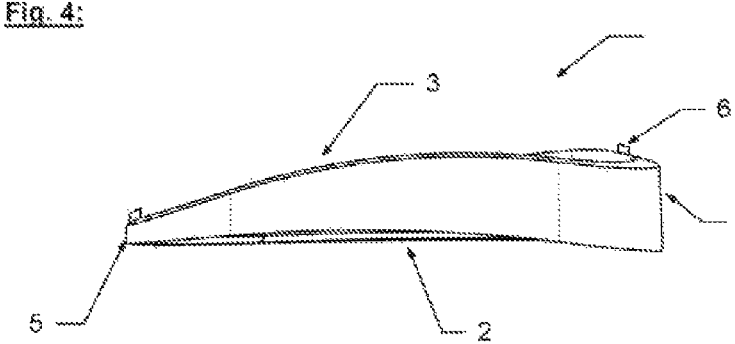
FIG. 4 shows a side view of an adapter ring 1 according to the invention.
Figure 5:
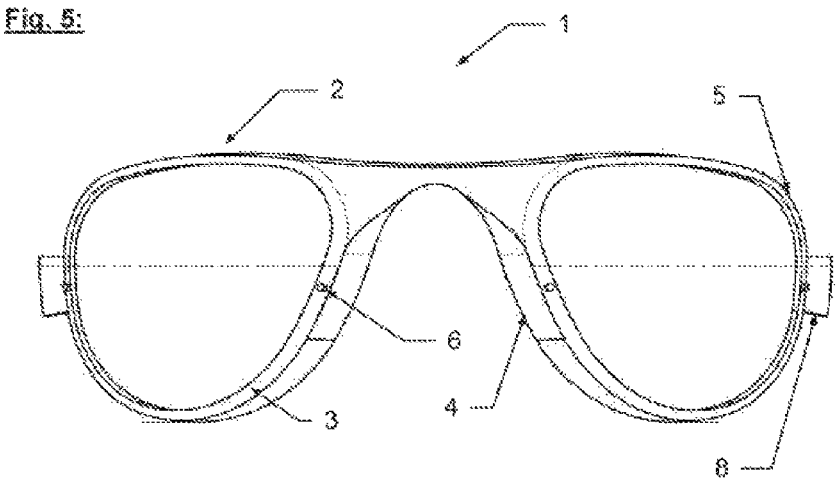
FIG. 5 shows a front view of the adapter rings 1 according to the invention in the form of adapter bodies connected by a bridge 9.
Figure 6:
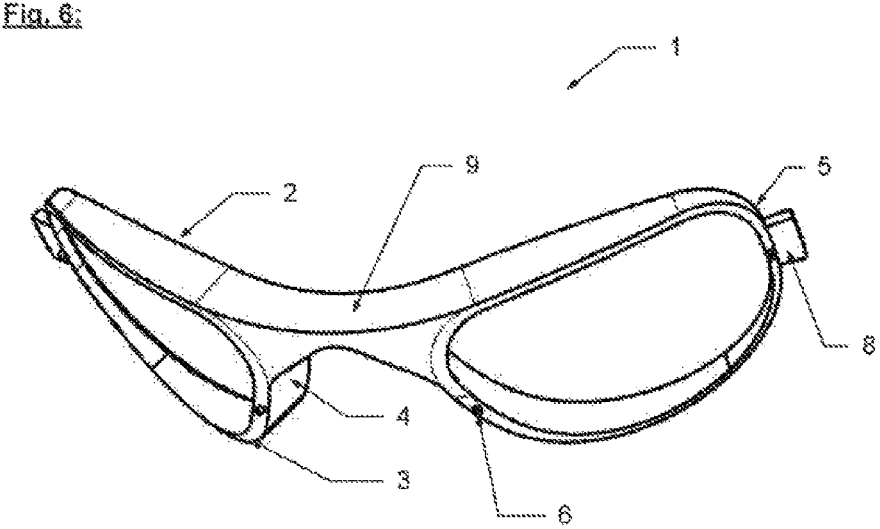
FIG. 6 shows a perspective view of the adapter body with connecting bridge 9.
Figure 7:
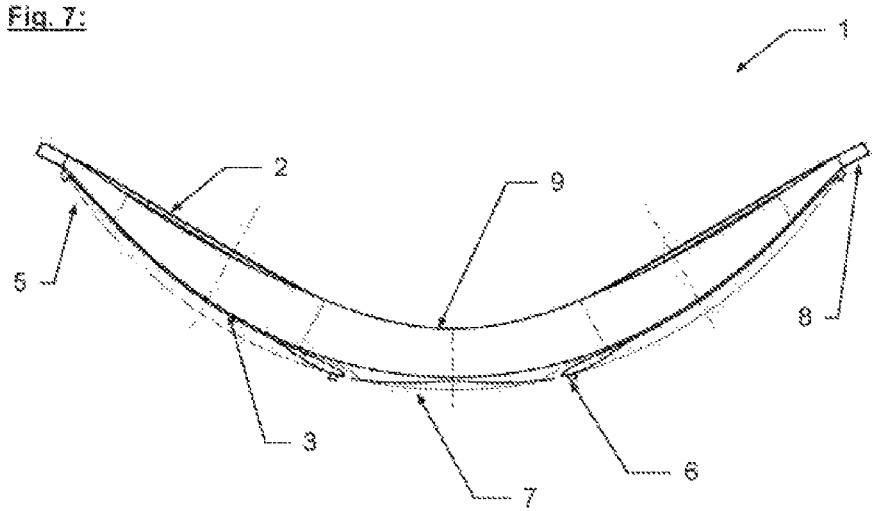
FIG. 7 shows a plan view of the adapter body with bridge 9.

It is basically the case here that FIGS. 1-4 represent the adapter rings 1 as single entities, to be fastened in protective glasses, whereas FIGS. 5-7 show adapter rings 1 which are connected by means of a connecting bridge 9 to form a common adapter body.

Figure 1:
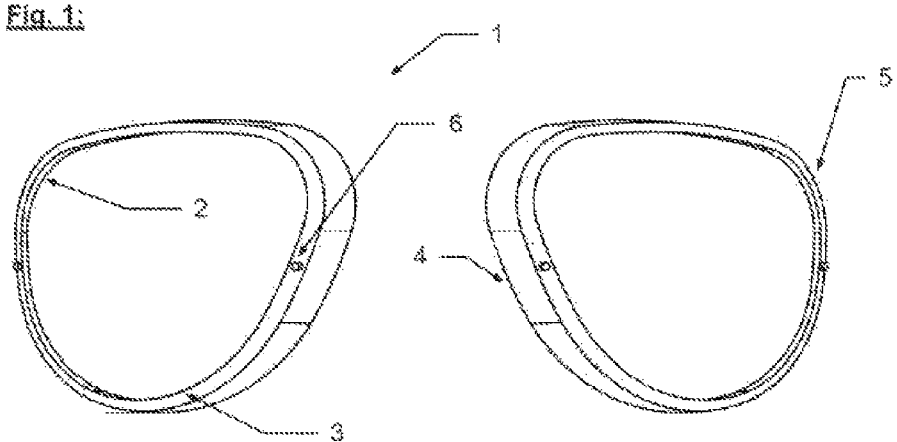
FIG. 1 shows a front view of the adapter rings 1 according to the invention.
Figure 2:
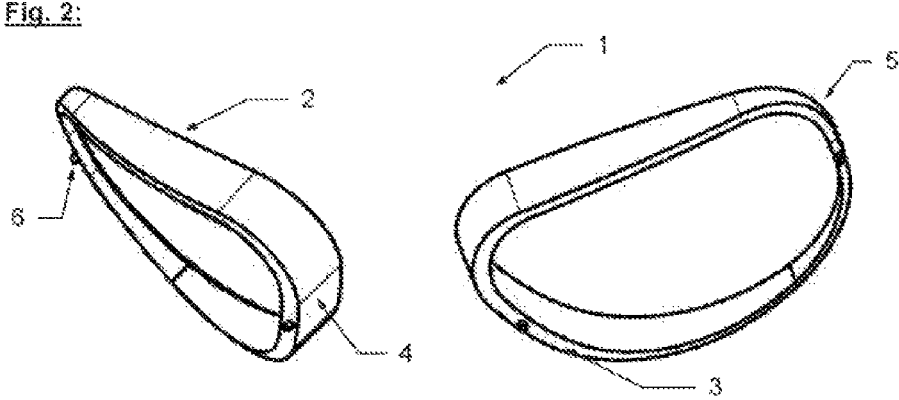
FIG. 2 shows a perspective view of the adapter rings 1 according to the invention from above.

It can be seen in FIGS. 1-4, in particular by way of FIGS. 2-4, that the present adapter rings 1 are complex components of which the curvatures have the task of performing different functions. It is clear here, in particular in FIGS. 2-4, that the rear curvature 2 does not run parallel to the front curvature 3 of the adapter rings 1; rather, the adapter-ring curvatures 3 here, which are oriented in the direction of the protective glasses, have more pronounced radii of curvature than the planar curvatures 2 of the facet for accommodating the correction lens.

The figures additionally show, in the front region, that connecting bodies 6 are arranged here on the front encircling edge of the adapter rings 1, said connecting bodies allowing defined positioning and fastening of the adapter rings 1 on the protective glasses. This is expedient since the adapter rings 1 are designed to be adapted specifically to the curvature of the protective glasses, and planar sealed abutment against the protective glasses is possible only when the adapter ring 1 has its position defined precisely.

It can also be seen that the adapter rings 1, rather than being designed in the form of a uniform body, have an approximately wedge-shaped cross section, as can be seen to good effect, in particular, in FIG. 3. FIG. 3 clarifies the arrangement of the adapter rings in their installed position, wherein the line 7 illustrates the progression of the lens of the protective glasses.

It is clear from this that the adapter rings 1, on account of their wedge-shaped design, give a projected development of the correction lenses in the direction of the plane of vision of the person wearing the protective glasses. This is achieved by a thickening of the adapter rings 1 in the nose region 4 and a tapering of the adapter rings 1 in the temple region 5. It can also be seen that the rear side 2 of the adapter rings 1, said rear side being directed toward the eye of the person wearing the glasses and being intended for accommodating the facet of the correction lens which is to be inserted, is considerably more planar than the front side 3.

The second embodiment of FIGS. 5-7, illustrated as an alternative, has a similar effect, on first glance, to a known glasses frame, although it is also the case here that the adapter rings 1 have the same function as described above. Here too, there is a thickening in the direction of the nose region 4 and a tapering toward the temple region 5.

Provision is additionally made for the correction lenses to be inserted into the rear mount of the standard-design curvature 2 for accommodating the facet of the correction lens which is to be inserted. This is a clear distinction from conventional glasses frames, in the case of which the correction lenses are inserted into the front side of the frame and not the rear side, as in this inventive solution. Here too, the intention is for the adapter ring 1, as has already been alluded to, to constitute an adapter in order to provide for compensation between the extreme curvature of the protective glasses, and of the protective-glasses lens, and the correction lenses used.

A quite significant difference from commercially available glasses frames is, in addition, that, in contrast to the conventionally used thermoplastic materials, the adapter rings 1 or the adapter body have to/has to be produced from a rigid, non-thermoplastic material with thermosetting properties. The background to this is that, in contrast to the conventional method, in which a lens is fitted into a glasses frame such that the glasses frame can be deformed thermoplastically by heating and thus allows lenses with different facets to be inserted into one and the same glasses frame.

In contrast to this, the basic inventive idea of the protective glasses here means that the adapter, whether in ring form or in the form of a complete body, has to be of non-deformable and stiff design, for which reason, as already described, a facet mount has to be arranged for precise fitting purposes in the rear of the adapter rings, and therefore it is possible for correction lenses which likewise all have to have identical facets to be inserted into said glasses frame.

This means that it is possible, in this way, for different types of lens to be inserted into one and the same adapter ring 1, since these types of lens are designed with identical facets. Likewise always identical in the case of the adapter ring is the curvature in the direction of the protective glasses, since this allows secure fitting in adaptation to the protective glasses.

The invention claimed is:

1. Protective glasses which have correction lenses and in the case of which retaining-frame-like connecting means are arranged in or on the protective glasses for the purpose of accommodating the correction lenses,
wherein
adapter rings are arranged as compensating bodies between a curvature of an outer contour of the protective glasses, in the region where the correction lenses are arranged, and a curvature of the correction lenses inserted, said adapter rings having, on their outer side, the curvature of the outer contour of the protective glasses, and having, on the opposite, inner side, the standard and identical curvature of the facet of the correction lens which is to be inserted, wherein the correction lenses of different thicknesses are coordinated at their circumferences so that their curvatures and shaping uniformly fit precisely with the adapter rings, and the likewise uniform curvature and shaping thereof, and are insertable in a defined position into the adapter rings, wherein the adapter rings are of such a depth that different thicknesses of correction lenses are insertable into the adapter rings, into the space between the outer contour of the protective glasses and the inner curvature of the adapter rings, wherein the adapter rings, being of approximately wedge-shaped design, are each thicker in the nose region and taper at the temple, wherein the adapter rings are designed in the form of an integral constituent part of the protective glasses, wherein the adapter rings are made of a rigid, non-thermoplastic material with thermosetting properties, and wherein the adapter rings are incorporated directly in apertures in the protective glasses.

2. The protective glasses which have correction lenses as claimed in claim 1,
wherein
the protective glasses are produced from non-thermoplastic materials.

3. The protective glasses which have correction lenses as claimed in claim 1,
wherein
the correction lenses are adhesively bonded or welded to the adapter rings.

4. The protective glasses which have correction lenses as claimed in claim 1,
wherein
the adapter ring has mounts and/or protrusions, which correspond with mounts and/or protrusions in the region of connection to the protective glasses such that the position of the adapter rings on the protective glasses is defined thereby.

5. The protective glasses which have correction lenses as claimed in claim 1,
wherein
the adapter rings are connected to one another by means of a bridge.

6. The protective glasses which have correction lenses as claimed in claim 5,
wherein
the lenses of the protective glasses, designed in one or more parts, are arranged on the adapter rings connected by a bridge.

7. The protective glasses which have correction lenses as claimed in claim 1,
wherein
ear pieces or retaining straps for providing a secure fit on the face are arranged in the temple region on the lenses of the protective glasses or on the adapter rings.

8. Protective glasses which have correction lenses and in the case of which retaining-frame-like connecting means are arranged in or on the protective glasses for the purpose of accommodating the correction lenses,
wherein
adapter rings are arranged in the form of compensating bodies between the curvature of the outer contour of the protective glasses, in the region where the correction lenses are arranged, and the curvature of the correction lenses inserted, said adapter rings having, on their outer side, the curvature of the outer contour of the protective glasses,
and having, on the opposite, inner side, the standard and identical curvature of the facet of the correction lens which is to be inserted,
wherein the correction lenses of different thicknesses are coordinated at their circumferences so that their curvatures and shaping uniformly fit precisely with the adapter rings, and the likewise uniform curvature and shaping thereof, and are insertable in a defined position into the adapter rings,
wherein the adapter rings are of such a depth that different thicknesses of correction lenses are insertable into the adapter rings, into the space between the outer contour of the protective glasses and the inner curvature of the adapter rings,
wherein each adapter ring, being of approximately wedge-shaped design, is thicker in the nose region and tapers at the temple,
wherein the adapter rings are designed in the form of an integral constituent part of the protective glasses,
wherein the adapter rings are made of a non-thermoplastic material, and
wherein the adapter rings are incorporated directly in apertures in the protective glasses.

* * * * *